United States Patent [19]

Schneider et al.

[11] 4,235,819
[45] Nov. 25, 1980

[54] PROCESS FOR ISOLATING 1-(ALKOXYPHENYL)-5-(PHENYL)BIGUANIDE COMPOUNDS FROM A CRUDE, ACID REACTION MIXTURE THEREOF

[75] Inventors: Louis Schneider, Elizabeth; Bruce M. Resnick, West Paterson, both of N.J.

[73] Assignee: GAF Corporation, New York, N.Y.

[21] Appl. No.: 37,926

[22] Filed: May 10, 1979

[51] Int. Cl.³ .......................................... C07C 129/16
[52] U.S. Cl. ................................................ 260/235
[58] Field of Search ........................................ 260/565

[56] References Cited

U.S. PATENT DOCUMENTS

| 2,704,710 | 1/1979 | Sprung | 260/565 |
|---|---|---|---|
| 3,996,232 | 12/1976 | Diamond et al. | 260/565 |
| 4,137,332 | 1/1979 | Brown et al. | 424/326 |

FOREIGN PATENT DOCUMENTS 716560  10/1954  United Kingdom ............... 260/565

OTHER PUBLICATIONS

Wheeler Henry, et al., "On a Class of Pseudothioureas Described as Normal Ureas." J. A. C. S. vol. 25 (1903) pp. 719-722.

*Primary Examiner*—Natalie Trousof
*Assistant Examiner*—L. Hendriksen
*Attorney, Agent, or Firm*—Walter C. Kehm; Walter Katz

[57] ABSTRACT

The present invention provides an improved process of isolating purified, free 1-(alkoxyphenyl)-5-(phenyl)-biguanide compounds, from a crude acid reaction mixture thereof. The compounds have the formula:

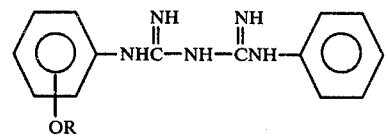

where R is alkyl, linear of branched, having from 1-14 carbon atoms, and are useful as agricultural fungicides.

The process comprises neutralizing the crude acid reaction mixture with aqueous base to precipitate the crude, free biguanide, filtering, slurrying the precipitate with a purification solvent which is an aliphatic hydrocarbon straight chain or branched, having from 5-10 carbon atoms, or mixtures thereof, filtering the slurry, and, drying the solid. Hexane is preferred as the purification solvent.

9 Claims, No Drawings

PROCESS FOR ISOLATING 1-(ALKOXYPHENYL)-5-(PHENYL)BIGUANIDE COMPOUNDS FROM A CRUDE, ACID REACTION MIXTURE THEREOF

BACKGROUND OF THE INVENTION

1. Field of the Invention

This invention relates to 1-(alkoxyphenyl)-5-(phenyl)biguanide compounds which are useful as agricultural fungicides, and, more particularly, to an improved process of isolating purified, free biguanide compounds from a crude acid reaction mixture thereof.

2. Description of the Prior Art

U.S. Pat. No. 4,137,332 disclosed 1-(alkoxyphenyl)-5-(phenyl) biguanide compositions for use as agricultural fungicides. However, the process of isolation and purification given therein for such compounds is not suitable for commercial manufacture of these compounds.

RELATED COPENDING PATENT APPLICATIONS

U.S. patent application Ser. No. 033,244, filed Apr. 25, 1979 (FDN-1178) claims a novel method of making the biguanide compounds herein as the acid addition salts and a different process for isolating purified free biguanides.

SUMMARY OF THE INVENTION

The present invention provides an improved process of isolating purified, free fungicidal 1-(alkoxyphenyl)-5-(phenyl)biguanide compounds having the formula:

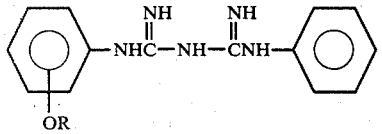

where R is alkyl, linear or branched, having from 1–14 carbon atoms, from a crude acid reaction mixture thereof.

Preferably, R is a linear alkyl group having from 6–12 carbon atoms, in the para position, and most preferably, R is $C_8$. A particularly effective compound is 1-(p-n-octaoxyphenyl)-5-(phenyl)biguanide.

The process comprises neutralizing the acid reaction mixture with aqueous base to precipitate the free biguanide, filtering, slurrying the precipitate with a purification solvent which is an aliphatic hydrocarbon, straight chain or branched, having from 5–10 carbon atoms, or mixtures thereof, filtering the slurry, and drying the solid. Hexane is the preferred purification solvent. The isolation and purification process herein recovers at least 80% of purified, free biguanide base from the crude acid reaction mixture.

DETAILED DESCRIPTION OF THE INVENTION

A suitable method for preparing the starting material, which is a crude acid reaction mixture of the biguanide, is illustrated in the chemical flow chart which follows hereinafter. Other synthetic routes may be used as well, however.

SYNTHESIS OF BIGUANIDE COMPOUNDS

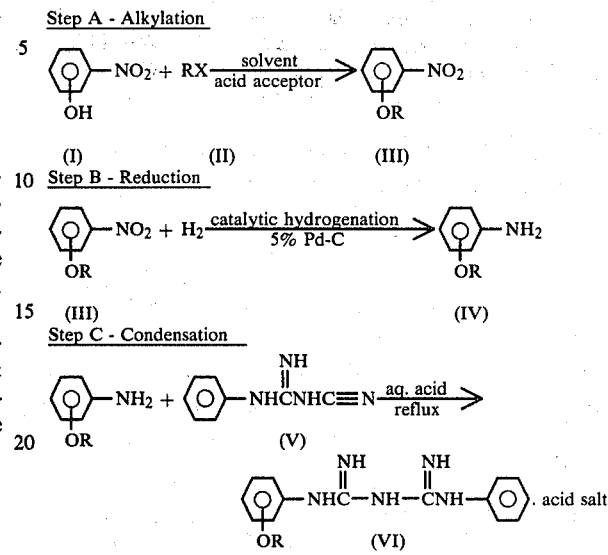

Step A in the process involves alkylation of a nitrophenol (I) with an alkyl halide (II) to provide an alkoxynitrobenzene (III). The alkyl halide has the formula RX, where R is a linear or branched alkyl group having from 1–14 carbon atoms, preferably from 6–12 carbon atoms, and, optimally, 8 carbon atoms. X is a halogen, e.g. chloro, bromo or iodo, and, preferably, chloro or bromo. The nitrophenol can have the nitro and hydroxy groups either ortho, meta or para to each other. The para position is preferred. Both starting reactants are commercially available or may be readily prepared by known methods.

The reaction is run in a suitable reaction solvent, preferably one in which at least one of the reactants is soluble, and optimally, in which both are soluble. Suitable reaction solvents include such known solvents as dimethylformamide, methylpyrrolidone, dimethylsulfoxide, toluene and the like. The preferred solvent is dimethylformamide. The reaction mixture includes an acid acceptor, such as a mild base, for example, potassium carbonate, which can absorb the acid-by-product of the alkylation. The reactants usually are present in about equal molar amounts, and the reaction is run at a somewhat elevated temperature, e.g. about 100°–150° C.

After completion of the reaction, the salts by-products preferably are filtered and washed with additional solvent. The mother liquor then is used as the in situ reactant for the next step, and the solvent washes are recycled to the next batch as the reaction solvent.

Step B in the process involves reduction by hydrogenation of the nitro group of the alkoxynitrobenzene intermediate (III) in situ to the corresponding amino group to provide an alkoxyaniline (IV). By carrying out the reduction step in the same solvent as used in the alkylation step, it is not necessary to isolate intermediate (III) during Step A, except for removal of the salts by filtration. Furthermore, hydrogenation can be effected at rather high concentrations of (III) to solvent; for example, concentrations upwards of 45% have been used very successfully. Preferably, catalytic hydrogenation is employed, using, e.g. 5% palladium-on-carbon at about 75°–80° C. at a pressure of 75–80 psig.

Step C in the process involves condensation of the alkoxyaniline (IV) with phenyldicyandiamide (V) to provide the desired 1-(alkoxyphenyl)-5-(phenyl) biguanide. Phenyldicyandiamide reactant is prepared by reacting sodium dicyanamide with diazotized aniline under alkaline conditions in water, and acidifying the triazene intermediate, as described in J. Am. Chem. Soc. 25, 719 (1903).

The condensation preferably is carried out in aqueous acid in alcohol solvent at reflux temperatures for several hours. Generally hydrochloric acid is used, although other inorganic and organic acids, such as hydrobromic acid, hydroiodic acid, sulfuric acid, nitric acid, phosphoric acid, acetic acid, methyl sulfuric acid, benzene sulfonic acid, and p-toluene sulfonic acid may be used as well. The product of the condensation is the crude acid addition salt of the biguanide compound (VI).

The crude acid addition salt (VI) then is neutralized directly with aqueous base to precipitate the crude free biguanide base. This base then is purified by slurrying with a suitable purification solvent to solubilize the organic impurities without dissolving the biguanide. Hydrocarbons, either straight chain or branched, or mixtures thereof, having about 5-10 carbon atoms, are preferred for this purpose. Hexane is considered an optimum purification solvent in this procedure. The slurry then is filtered and the purified free biguanide base is isolated after further washing with hexane and drying in a vacuum oven.

EXAMPLE 1

Synthesis of 1-(p-n-Octaoxyphenyl)-5-(Phenyl)Biguanide Hydrochloride

(a) p-Octaoxynitrobenzene

Into a 2 l. flask was charged a mixture of p-nitrophenol (278 g., 2.0 mole), chlorooctane (310.8 g., 2.09 mole), potassium carbonate (145.2 g., 1.05 mole) in dimethylformamide (DMF) (556 g.) as a solvent. The reaction mixture then was heated at 130°-135° C. for 4 hours. The progress of the reaction was monitored by gas-liquid chromatography (glc) analysis. The residue salts then were filtered and washed twice with 400 cc. of DMF. The mother liquor, which weighed 967 g., contained 442 g. of the desired intermediate. The combined washes, which weighed 963 g., contained an additional 52.1 g. of product. The total yield of intermediate was 494.3 g. of 98% purity, or 484.4 g. of the compound (96.5% yield). The DMF washes were recycled to the next batch as the reaction solvent.

(b) p-Octaoxyaniline

Into a 1 l. pressure reactor was charged the reaction product from step (a) above, namely, 600 cc of a 46% solution of p-octaoxynitrobenzene in DMF (587 g., 1.07 mole) and 3.8 g. of 5% palladium-on-carbon catalyst. The reactor then was purged three times with nitrogen at room temperature at a pressure of 60 psig and then twice with hydrogen at the same pressure. The reactor temperature then was raised to 80° C. and hydrogen was admitted to maintain a constant pressure of 75-80 psig for 5 hrs. with intermittent heating and cooling. Finally, the reaction mixture was cooled to 25° C., vented, purged with nitrogen, and the catalyst separated by filtration.

The DMF solvent then was stripped under vacuum at 50-75 mm at a pot temperature of 67°-105° C. A total of 327 g. (95%) of the solvent was recovered for recycling to step (a) as the wash solvent. The yield of crude product was 243 g. (95.4% purity by glc analysis).

(c)

Into a 2 l. flask was charged p-octaoxyaniline (243 g., 91% purity, 1.0 mole) and 980 cc of ethanol. Thereafter, during a ½ hour period at 25°-30° C., a total of 109.7 g. of concentrated hydrochloric acid was added followed by phenyldicyandiamide (176.0 g., 1.1 mole). The reaction mixture then was heated at a reflux temperature of 75° C. for 6 hours. The reaction product was cooled to ice-bath temperature and filtered to give 390 g. of a solid product (93.5% yield) m.p. 114°-118° C.

(d) Isolation and Purification

The crude reaction product of step (c) was neutralized by drowning it into 2550 cc of 2% aqueous sodium hydroxide maintained at 45°-50° C. The crude, neutralized biguanide then was agitated for 1 hr. at 45°-50° C., cooled to 25°-30° C., filtered and water washed until the pH of the filtrate was 7.5-8.0. The crude wet cake weighed 784 g., which contained about 352.8 g. of product on a dry basis (92.6% crude yield).

The crude product then was slurried with 1200 cc of hexane at 25°-30° C. for ¼ hr., filtered, and washed with an additional 600 cc of hexane. The thus-purified free biguanide base was dried in a vacuum oven at 50° C. The purified free biguanide base weighed 298 g. (78.2% yield from the p-octaoxyaniline). The melting point was 120°-121° C.

What is claimed is:

1. An improved process of isolating purified free 1-(alkoxyphenyl)-5-(phenyl)biguanide compounds having the formula:

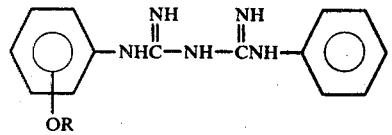

where R is alkyl, linear or branched, having from 1-14 carbon atoms, from a crude acid reaction mixture thereof containing the impure compound, prepared by alkylation of a nitrophenol, reduction to the alkoxyaniline, and condensation in acid with phenyldicyandiamide, which comprises neutralizing said acid mixture with aqueous base to the crude, free biguanide, filtering, slurrying the precipitate with an aliphatic hydrocarbon purification solvent, straight chain or branched, having from 5-10 carbon atoms, or mixtures thereof to remove impurities, filtering the slurry, and, drying the solid.

2. A process according to claim 1 wherein said purification solvent is hexane.

3. A process according to claim 1 wherein at least 80% of biguanide is recovered as purified free biguanide from said crude acid reaction mixture.

4. A process according to claim 1 wherein said neutralization is carried out with sodium hydroxide at about 45°-50° C./. and said crude free biguanide is filtered at about 25°-30° C.

5. A process according to claim 1 wherein said drying is carried out at about 50° C. in a vacuum oven.

6. A process according to claim 1 wherein R is alkyl having 7-12 carbon atoms.

7. A process according to claim 1 wherein RO is located in the para position of the ring.

8. A process according to claim 1 wherein RO is the p-n-octaoxy group.

9. A process according to claim 1 wherein said acid salt is the hydrochloride.

* * * * *